United States Patent
Porter et al.

(10) Patent No.: US 8,021,340 B2
(45) Date of Patent: Sep. 20, 2011

(54) ENHANCED APPARATUS FOR PERCUTANEOUS CATHETER IMPLANTATION AND REPLACEMENT

(75) Inventors: Christopher H. Porter, Woodinville, WA (US); Claude A. Vidal, Santa Barbara, CA (US); Russell J. Redmond, Goleta, CA (US); Byron L. Moran, Santa Barbara, CA (US); Abram D. Janis, Valencia, CA (US); Kelly A. Chapman, Altadena, CA (US)

(73) Assignee: Incumed, LLC, Valencia, CA (US)

( * ) Notice: Subject to any disclaimer, the term of this patent is extended or adjusted under 35 U.S.C. 154(b) by 357 days.

(21) Appl. No.: 12/321,962

(22) Filed: Jan. 26, 2009

(65) Prior Publication Data

US 2009/0171295 A1   Jul. 2, 2009

Related U.S. Application Data

(63) Continuation-in-part of application No. 12/287,130, filed on Oct. 6, 2008, and a continuation-in-part of application No. 11/708,445, filed on Feb. 20, 2007, now Pat. No. 7,731,697.

(60) Provisional application No. 60/818,768, filed on Jul. 5, 2006, provisional application No. 60/999,480, filed on Oct. 17, 2007.

(51) Int. Cl.
*A61M 5/32* (2006.01)

(52) U.S. Cl. ...................................................... 604/175

(58) Field of Classification Search .................. 604/175, 604/177–178
See application file for complete search history.

(56) References Cited

U.S. PATENT DOCUMENTS

| 3,447,161 A | 6/1969 | Weikel |
| 3,683,911 A | 8/1972 | McCormick |
| 3,783,868 A | 1/1974 | Bokros |
| 4,147,164 A | 4/1979 | Behney |
| 4,278,092 A | 7/1981 | Borsanyi et al. |
| 4,379,506 A | 4/1983 | Davidson |
| 4,417,888 A | 11/1983 | Cosentino et al. |
| 4,488,877 A | 12/1984 | Klein et al. |
| 4,496,349 A | 1/1985 | Cosentino |

(Continued)

FOREIGN PATENT DOCUMENTS

EP        0367354        2/1993

(Continued)

*Primary Examiner* — Nicholas D Lucchesi
*Assistant Examiner* — Melissa A Snyder
(74) *Attorney, Agent, or Firm* — Arthur Freilich (57) ABSTRACT

A medical apparatus and method of use for implanting a percutaneous catheter in a patient's body which catheter can be easily positioned, repositioned, and replaced. The apparatus includes an elongate sleeve having a tapered forward portion to facilitate its insertion through an undersized incision. The sleeve provides an interior elongate passageway which extends from a sleeve proximal end to a sleeve distal end. The sleeve is intended to be percutaneously implanted through an incision in the patient's skin so that the sleeve distal end resides subcutaneously. The sleeve outer peripheral surface carries a layer of porous material intended to be placed under the patient's outer skin layer in contact with the dermis to promote tissue ingrowth for anchoring the sleeve and forming an infection resistant barrier. The sleeve passageway is dimensioned to snugly accommodate the outer surface of catheter while permitting the catheter to slide relative to the sleeve. A sealing device is mounted around the catheter adjacent to the sleeve proximal end to prevent deleterious material from migrating into the patient's body along the catheter outer surface. A locking member secured to the sleeve can be pivoted to an unlocked portion for permitting axial and rotational movement of said catheter relative to said sleeve and or to a locked position for preventing such relative movement.

16 Claims, 5 Drawing Sheets

U.S. PATENT DOCUMENTS

| | | |
|---|---|---|
| 4,540,411 A | 9/1985 | Bodicky |
| 4,592,749 A | 6/1986 | Ebling et al. |
| 4,648,391 A | 3/1987 | Ellis |
| 4,668,222 A | 5/1987 | Poirier et al. |
| 4,728,331 A | 3/1988 | Russier |
| 4,729,366 A | 3/1988 | Schaefer |
| 4,781,693 A | 11/1988 | Martinez et al. |
| 4,781,694 A | 11/1988 | Branemark et al. |
| 4,828,560 A | 5/1989 | Heyler, III |
| 4,886,502 A | 12/1989 | Poirier et al. |
| 4,897,081 A | 1/1990 | Poirier et al. |
| 5,007,897 A | 4/1991 | Kalb et al. |
| 5,041,085 A | 8/1991 | Osborne et al. |
| 5,085,646 A | 2/1992 | Svenson et al. |
| 5,098,434 A | 3/1992 | Serbousek |
| 5,109,875 A | 5/1992 | Gottlieb |
| 5,221,263 A | 6/1993 | Sinko et al. |
| 5,318,040 A | 6/1994 | Kensey et al. |
| 5,360,397 A | 11/1994 | Pincuck |
| 5,370,698 A | 12/1994 | Heimke et al. |
| 5,407,354 A | 4/1995 | Fife |
| 5,411,467 A | 5/1995 | Hortmann et al. |
| 5,715,815 A | 2/1998 | Lorenzen et al. |
| 5,885,217 A | 3/1999 | Gisselberg et al. |
| 5,931,838 A | 8/1999 | Vito |
| 6,099,508 A | 8/2000 | Bousquet |
| 6,332,874 B1 | 12/2001 | Eliasen et al. |
| 6,334,862 B1 | 1/2002 | Vidal et al. |
| 6,520,939 B2 | 2/2003 | Lafontaine |
| 6,544,206 B1 | 4/2003 | Johnston, Jr. |
| 6,896,689 B2 | 5/2005 | Gedebou |
| 6,916,310 B2 | 7/2005 | Sommerich |
| 6,955,677 B2 | 10/2005 | Dahners |
| 2002/0072712 A1 | 6/2002 | Nool et al. |
| 2002/0107475 A1 | 8/2002 | Maginot |
| 2003/0149422 A1 | 8/2003 | Muller |
| 2003/0199827 A1 | 10/2003 | Thorne |
| 2004/0111138 A1 | 6/2004 | Bleam et al. |
| 2004/0204686 A1 | 10/2004 | Porter et al. |
| 2005/0059925 A1 | 3/2005 | Maginot et al. |
| 2006/0030817 A1 | 2/2006 | Kraus et al. |
| 2007/0149949 A1 | 6/2007 | Porter et al. |
| 2007/0213675 A1 | 9/2007 | Albrecht et al. |
| 2008/0108969 A1 | 5/2008 | Kerr |

FOREIGN PATENT DOCUMENTS

| | | |
|---|---|---|
| GB | 2268066 A | 1/1994 |
| WO | WO93/15664 A1 | 8/1993 |

ENHANCED APPARATUS FOR PERCUTANEOUS CATHETER IMPLANTATION AND REPLACEMENT

RELATED APPLICATIONS

This application is a Continuation-In-Part of (1) U.S. application Ser. No. 11/708,445 filed on Feb. 20, 2007 now U.S. Pat. No. 7,731,697 which claims priority based on U.S. Provisional Application 60/818,768 filed on Jul. 5, 2006 and (2) U.S. application Ser. No. 12/287,130 filed on Oct. 6, 2008 which claims priority based on U.S. Provisional Application 60/999,480 filed on Oct. 17, 2007. This application claims priority based on the aforementioned applications which are by reference incorporated herein.

FIELD OF THE INVENTION

This invention relates generally to medical technology and more particularly to a method and apparatus for implanting an elongate conduit, e.g., a catheter or cable, to extend through a patient's skin for providing long term access to an interior body site. Embodiments of the invention are useful in a variety of applications, e.g., in hemodialysis procedures to enable a catheter to provide fluid access to a patient's central venous system and/or nerve stimulation procedures in which a cable provides access to an implanted electric device.

BACKGROUND OF THE INVENTION

In a variety of medical procedures, catheters are percutaneously implanted, i.e., through a patient's skin, to provide long term access to interior body sites; e.g., blood vessels and organs. Unless adequate precautions are taken, infections and inflammation can readily occur at the catheter entry site. To mitigate such problems, a tissue integrating cuff is sometimes attached to the catheter and placed under the patient's skin to resist infection. Although such a cuff can reduce the likelihood of infection, once ingrown its presence increases the difficulty of removing and/or repositioning an implanted catheter. More particularly, it is not uncommon for an implanted catheter to become damaged, e.g., clogged or kinked, over an extended period of use thus necessitating catheter removal and/or replacement. When this occurs, the cuff must be dissected thereby complicating and prolonging the surgical procedure.

The aforementioned parent application Ser. No. 11/708,445 describes a medical apparatus and method which enables an elongate conduit, e.g., a catheter or cable, to be percutaneously implanted in a manner which allows the conduit to be readily positioned, repositioned, and replaced. A preferred embodiment described in said parent application includes a sleeve carrying a tissue integrating porous layer proximate to the sleeve distal end. The sleeve distal end is intended for insertion through a skin incision to subcutaneously locate the porous layer in contact with the patient's dermis for promoting soft tissue ingrowth. Such tissue ingrowth functions to anchor the sleeve and create an infection resistant barrier. The preferred embodiment described in said parent application preferably also includes a protective sheath overlaying the porous layer to avoid injuring incision adjacent tissue as the sleeve distal end is inserted through the incision. The sheath is removed from the sleeve by the physician after the porous layer has passed through the incision.

The aforementioned parent application Ser. No. 12/287,130 describes an apparatus and method for implanting a medical device through an incision which is intentionally undersized relative to the lateral dimension, i.e., width or diameter, of the device porous layer to enhance cell proliferation and healing.

SUMMARY OF THE INVENTION

The present invention is directed to an enhanced medical apparatus embodiment for more conveniently percutaneously implanting an elongate conduit, e.g., a catheter or cable, in a manner which both avoids tissue injury as the apparatus is implanted and allows the conduit to be easily positioned, repositioned, and replaced. The apparatus includes an elongate tubular sleeve having a forward portion whose outer surface is tapered to dilate a patient's skin incision as the sleeve is inserted therethrough. The sleeve includes an interior axial passageway through which the conduit is able to slide.

A preferred embodiment in accordance with the present invention is particularly configured to simplify implantation and avoid injury to the patient's incision adjacent tissue. More particularly, the preferred embodiment includes an elongate tubular sleeve formed of biocompatible material, e.g., titanium, having a tapered forward portion, extending proximally from a sleeve distal end to a lateral shoulder surface. The tapered forward portion has a smooth outer surface which gradually increases in lateral dimension, i.e., width or diameter, from D1 near its distal end to D2 near the shoulder surface. A rearward sleeve portion extending proximally from the shoulder surface defines an outer lateral dimension D3, where D3 is less than D2. In accordance with the present invention, the rearward portion carries a layer of porous material, e.g., a biocompatible mesh, near the shoulder surface forming an outer diameter D4 where D4 is preferably slightly less than D2.

The aforedescribed configuration permits the sleeve to be implanted through a single minimally sized incision while avoiding injury to incision adjacent tissue which might otherwise be caused as the porous material passes through the incision. More particularly, it is preferable to provide an intentionally undersized incision (i.e., approximately 10-20% smaller than D4) for receiving the sleeve distal end, as is taught in applicant's aforementioned parent application Ser. No. 12/287,130. In use, as the sleeve forward portion is inserted through the incision, the smooth tapered surface gently elastically stretches, or dilates, the patient's adjacent tissue to a diameter D2 allowing the porous material to pass through the incision without abrading or otherwise injuring the incision adjacent tissue.

The sleeve interior axial passageway is dimensioned to snugly accommodate the outer surface of a conduit (which will hereinafter be assumed to be a catheter unless otherwise stated) while permitting the conduit to slide and rotate in the passageway relative to the sleeve. A sealing device within the sleeve extends around the catheter, e.g., near the sleeve proximal end, to prevent deleterious material from migrating into the patient's body along the catheter outer surface. The sealing device preferably comprises an annular seal formed of a soft flexible material, e.g., silicone, mounted within the sleeve passageway. The annular seal comprises a peripheral wall having an outer surface and an inner surface surrounding an interior bore. At least one annular flexible nib on the seal inner surface projects radially into the bore for sealing against the catheter outer surface. Although the sleeve preferably comprises a rigid titanium tube, alternatively, the sleeve can be formed of flexible tubing, e.g., silicone, allowing an interior annular sealing nib to be formed integral therewith.

The preferred embodiment also includes a locking member hinged to the anchor device mounted near the sleeve proximal end. The locking member can be readily pivoted between a first, or locked, position surrounding the conduit and a second, or unlocked, position remote from the conduit. In the unlocked position, the catheter is able to slide and/or rotate relative to the sleeve passageway. In the locked position, the locking member is able to apply a friction force to the catheter outer surface to prevent relative movement between the catheter and the sleeve. A preferred locking member comprises a split ring formed of a soft flexible material, e.g., silicone which, in the locked position, can be radially compressed to frictionally grip the catheter outer surface to prevent catheter movement relative to the sleeve. The split ring can be compressed in various ways; e.g., by simply tying it with suture thread or by using an internal or external clip, e.g., spring urged clamp, to pinch the split ring.

In a preferred procedure, a physician will make a controlled incision having a width approximately 10-20% less than D4, near the patient's chest or abdomen. A surgical tunneler tool is then typically inserted through the incision, to form a subcutaneous tunnel to an interior site through which a standard flexible catheter can be inserted and positioned. In accordance with the invention, the catheter carries the aforementioned sleeve and functions to guide the sleeve distal end through the undersized incision to place the sleeve porous layer in contact with the patient's dermis beneath the patient's outer skin surface. The sleeve proximal end is then preferably externally anchored to the patient's skin. With the locking member in its unlocked position, the physician is able to slide and/or rotate the catheter relative to the sleeve and locking member for optimum catheter tip positioning. When the catheter is properly positioned, the physician can then pivot the locking member to the locked position and then compress it to grip the catheter outer surface. With the sleeve thus implanted, the patient's subcutaneous tissue will, over time, grow into the porous material to anchor the sleeve and form an infection resistant barrier. The porous material, and/or sleeve interior, can be coated or impregnated with constituents having antimicrobial and/or anti-inflammatory properties, e.g., silver containing compounds or antibiotic eluting coatings and/or steroids, to further promote healing.

DETAILED DESCRIPTION

Various medical regimens relating, for example, to hemodialysis drug infusion, plasmapheresis, etc., use a percutaneously implanted conduit for conveying fluid and/or electric signals to/from an interior body site. The present invention is directed to a method and apparatus for facilitating the implantation and utilization of a percutaneous conduit (e.g., catheter) and for facilitating the positioning, repositioning, and replacement, or exchange, of the catheter.

Figure 1:
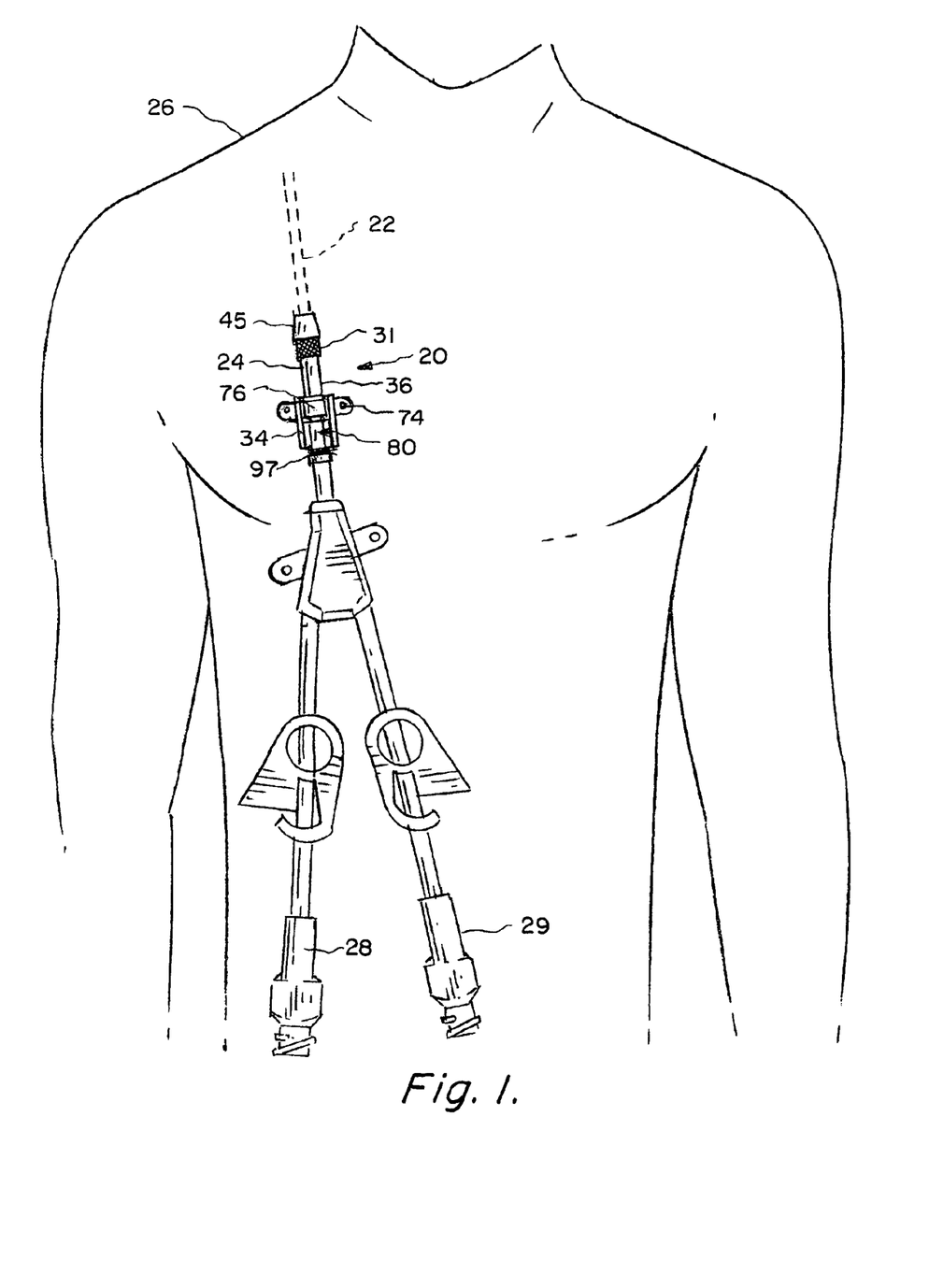
FIG. 1 is a schematic representation generally depicting a catheter assembly in accordance with the invention for percutaneously implanting a catheter for an exemplary hemodialysis application.

FIG. 1 schematically depicts an assembly 20 in accordance with the invention for percutaneously implanting a catheter 22 through an incision 24 in a patient 26 undergoing an exemplary hemodialysis procedure. In such a procedure, a dual lumen catheter 22 is typically used with the two lumens being respectively coupled to separate exterior flow couplers 28 and 29.

Figure 4:
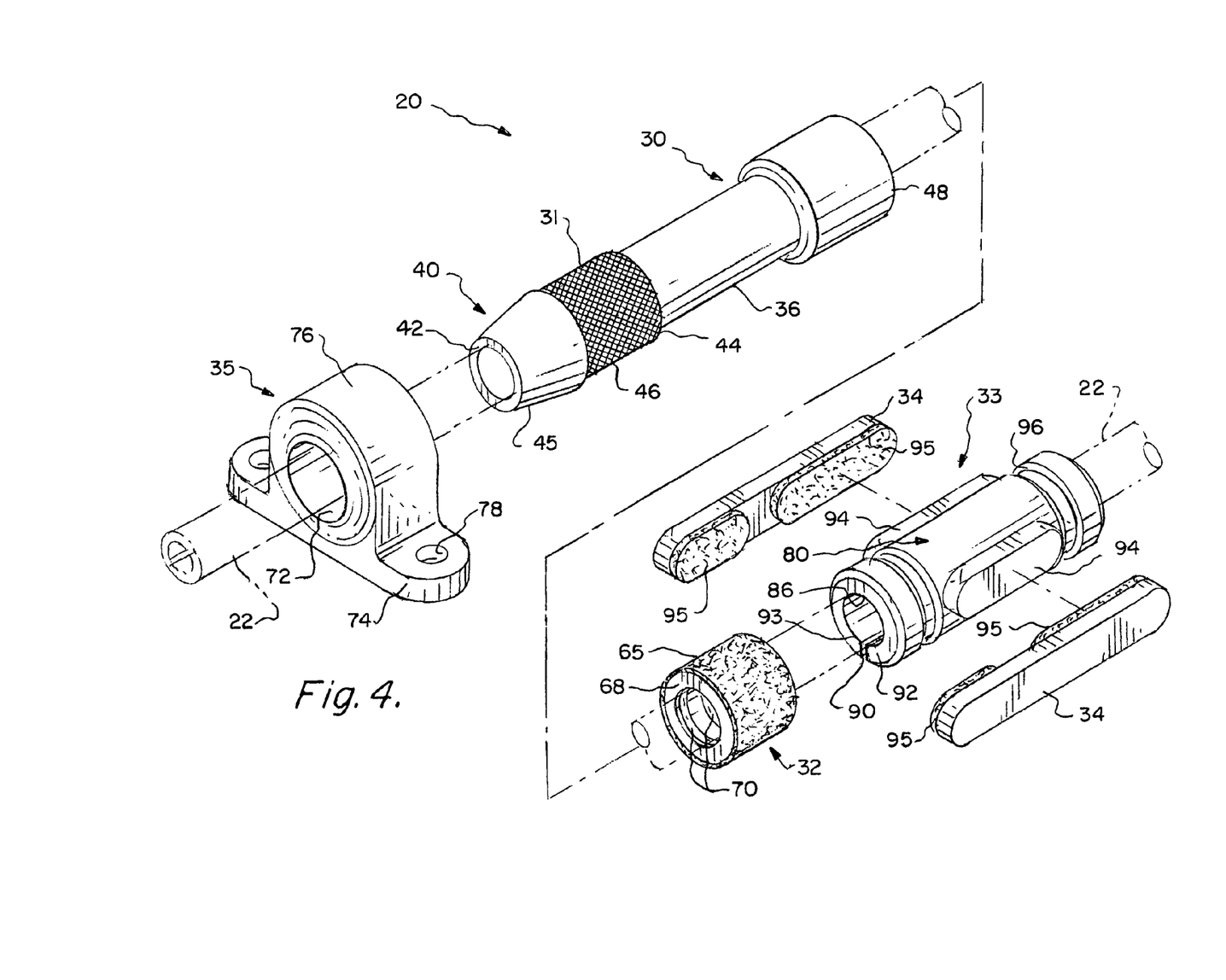
FIG. 4 is an exploded view of the assembly of FIG. 2 showing a catheter in phantom, an anchor, a sleeve carrying a layer of porous material, an annular seal, and a locking member.

Attention is now directed to FIGS. 2-5 which depict a preferred catheter assembly 20 in accordance with the present invention. FIG. 4 best shows the primary elements of the assembly 20 including sleeve 30 carrying a porous layer 31, a sealing device 32, a locking member 33, hinge members 34, and an anchor 35 for retaining the proximal end of sleeve 30 adjacent to a patients outer skin surface.

The sleeve 30 preferably comprises a substantially rigid tubular titanium member formed by a peripheral wall 36 having an outer surface 37 and an inner surface 38. As can be best seen in FIG. 5, the sleeve 30 outer surface 37 is shaped to define a tapered forward portion 40 proximate to the sleeve distal region, or end, 42 and a rearward portion 43 proximate to the sleeve proximal region, or end, 44. The tapered forward portion 40 has a smooth outer surface 45 which gradually increases in lateral dimension, or diameter, from D1 near the sleeve distal end 42 to D2 near shoulder surface 46. The sleeve rearward portion 43 is comprised of an axial section 47 having a uniform lateral dimension D3 distally of the shoulder surface 46 and a bulbous proximal section 48. A layer 31 of porous material is mounted around the sleeve just distally of the shoulder surface 46. The porous layer 31 defines a lateral dimension D4 where D4 is no greater than D2, but preferably slightly smaller than D2.

Figure 5:
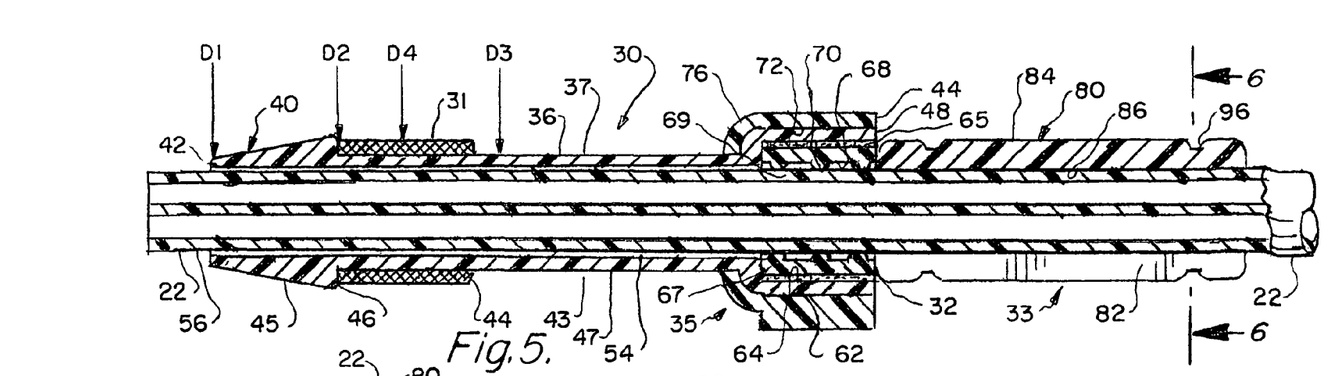
FIG. 5 is a sectional view taken substantially along the plane 5-5 of FIG. 2.
Figure 6:
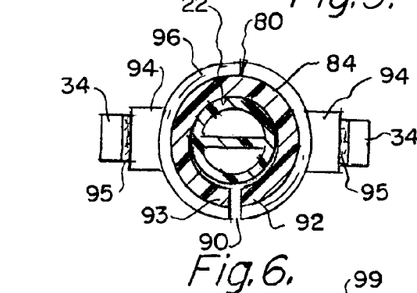
FIG. 6 is a sectional view taken substantially along the plane 6-6 of FIG. 5.

The sleeve inner surface 38 surrounds an interior passageway 54 extending axially from the sleeve proximal end 44 to the sleeve distal end 42. FIG. 5 shows the sleeve 30 mounted on the catheter 22 which extends axially through the passageway 54. The catheter outer surface 56 and passageway wall surface 38 are closely dimensioned but with sufficient clearance therebetween to enable the catheter to slide axially and rotate in the passageway 54. The sleeve 30 rearward portion 43 includes the aforementioned enlarged bulbous section 48 having an outer peripheral surface 62 and an inner peripheral surface 64 defining an interior recess for retaining the aforementioned sealing device 32 utilizing, for example, adhesive 65. The sealing device 32 preferably comprises an annular member 67 formed of a soft flexible material, e.g., silicone. The annular member 67 defines an inner peripheral surface 68 surrounding an interior bore 69 which is contiguous with sleeve passageway 54. At least one flexible annular nib 70 extends radially into the bore 69 for contacting and sealing against the catheter outer surface 56.

The outer peripheral surface 62 of bulbous section 48 is dimensioned to closely fit into bore 72 of anchor 35. The anchor 35 (FIG. 4) comprises a base portion 74 supporting a ferrule portion 76 which defines the bore 72. The anchor base portion 74 is provided with holes 78 to facilitate the suturing of anchor 35 to the patient's outer skin.

Figure 2:
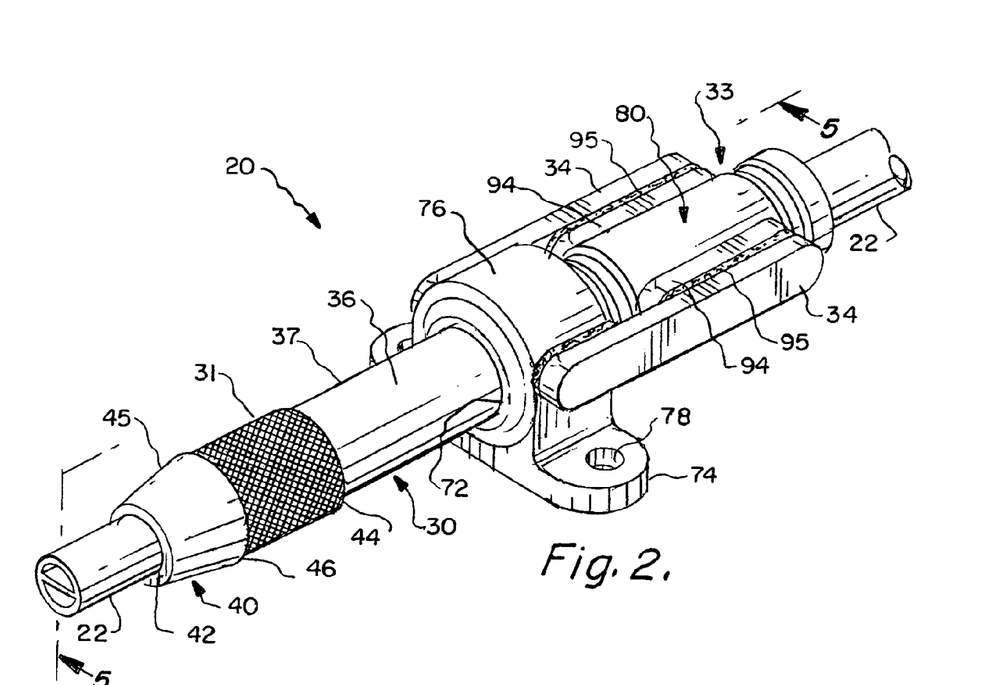
FIG. 2 is an isometric view of a preferred catheter assembly in accordance with the invention shown in its locked state.
Figure 3:
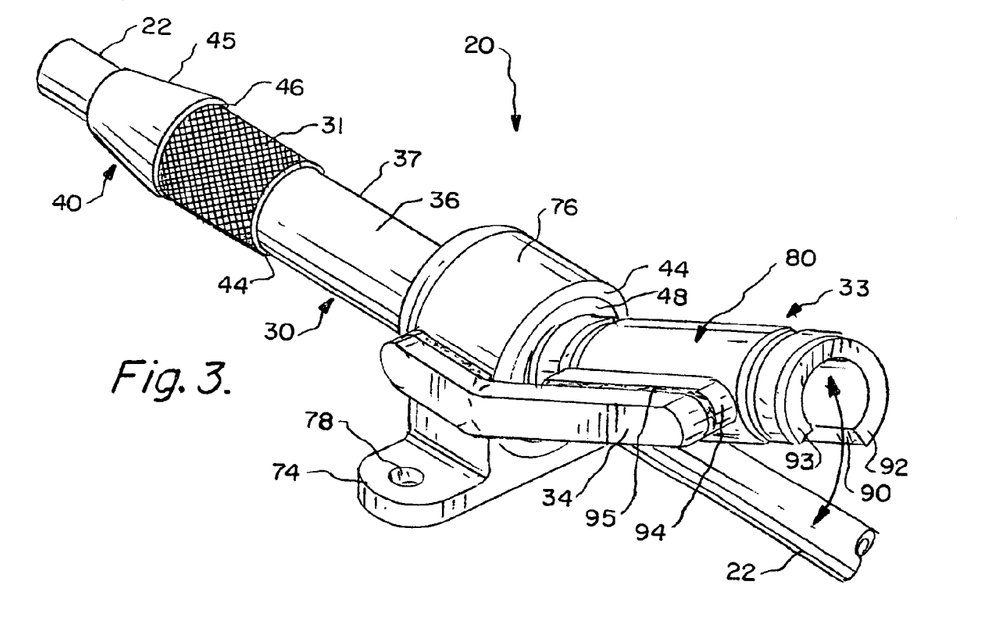
FIG. 3 is an isometric view of the preferred catheter assembly of FIG. 2 shown is its unlocked state.
Figure 7:
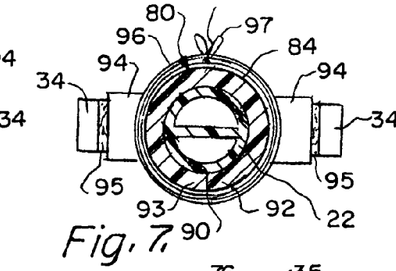
FIG. 7 is a sectional view similar to FIG. 6 but showing the locking member in its locked state clamped by suture wire.
Figure 8:
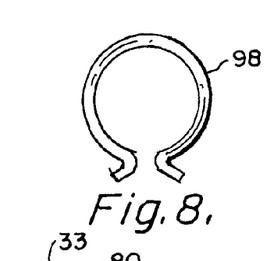
FIG. 8 shows an exemplary spring clip which can be alternatively used for clamping the locking member in its locked state.

The locking member 33 preferably comprises a split ring 80 formed of soft flexible material, e.g., silicone. More particularly, the locking member 33 is comprised of a peripheral wall 82 having an outer surface 84 and an inner surface 86 surrounding an interior bore. The wall 82 is longitudinally split at 90 to form opposed edges 92, 93. The wall outer surface 84 is preferably provided with one or more pads 94 for attaching the aforementioned hinge members 34, as by adhesive 95. The hinge members 34 preferably comprise flexible straps which are also adhered to the outer surface of anchor 35, as can be best seen in FIGS. 2 and 3. These hinge straps 34 allow the split ring 80 to pivot between a first, or locked, portion (FIG. 2) surrounding the catheter 22 and a second, or unlocked, position (FIG. 3) remote from the catheter. The locking member outer wall surface 84 is preferably provided with at least one proximal annular groove 96 for accommodating suture thread 97 (FIG. 7) or an appropriately shaped spring clip 98 (FIG. 8) which can be used by the physician to compress the split ring 80 and frictionally engage it around the catheter outer surface 56 when the locking member 33 is in its first position (FIG. 2).

Figure 9:
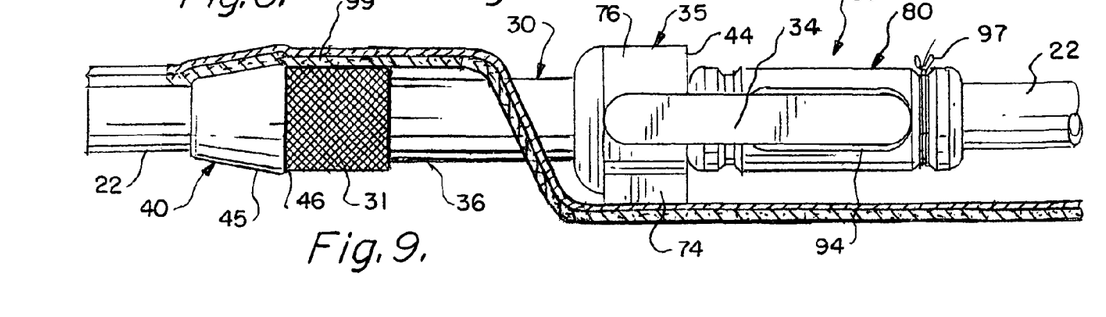
FIG. 9 shows a cross-sectional view of the catheter assembly as implanted with the porous layer positioned subcutaneously adjacent the patient's dermis.

In use, it is intended that the sleeve forward portion 40 be inserted through an incision 24 in the patient's skin to position the porous layer 31 beneath the patient's epidermis skin layer (FIG. 9) in contact with the patient's dermis layer 99 to promote soft tissue ingrowth. Over time, this tissue ingrowth acts to firmly anchor the sleeve 30 in place and to form an infection resistant barrier around the sleeve. This barrier may be enhanced by incorporating antimicrobial and/or anti-inflammatory constituents into the porous layer 31. For example, silver containing compounds and/or antibiotic eluting coatings can be used as antimicrobial agents and steroids can be used as anti-inflammatory agents.

A preferred catheter assembly in accordance with FIGS. 2-9 includes a sleeve 30 comprising a rigid titanium tube having exemplary dimensions as follows:

| | |
|---|---|
| Sleeve overall length | 1.485 inches |
| Forward portion length | 0.284 inches |
| passageway 54 ID | 0.200 inches |
| D1 | 0.237 inches |
| D2 | 0.330 inches |
| D3 | 0.250 inches |
| D4 | 0.308 inches |
| nib 70 ID | 0.178 inches |

In an alternative embodiment, the sleeve can be similarly dimensioned but instead of being formed of a rigid material such as titanium, can be formed of a flexible material such as silicone. In such an embodiment, the annular sealing nibs can be integrally formed with the sleeve.

Figures 10, 12, 13:
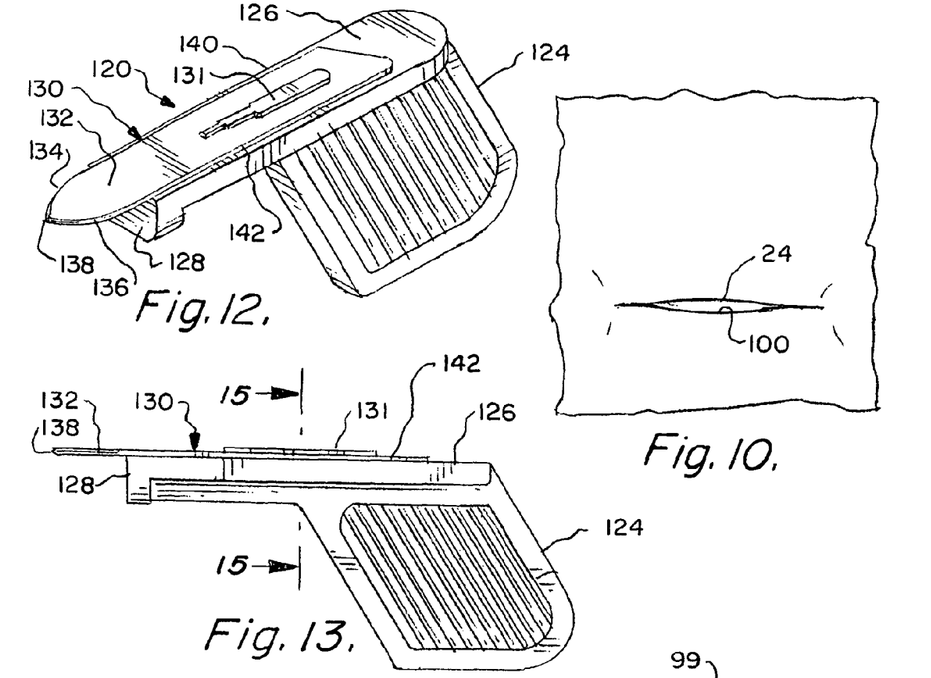
FIG. 10 is a drawing showing a dimensioned incision formed in accordance with the present invention.
FIG. 12 is an isometric view of an exemplary surgical cutting tool for forming the incision of FIG. 10.
FIG. 13 is a side view of the cutting tool of FIG. 12.
Figure 11:
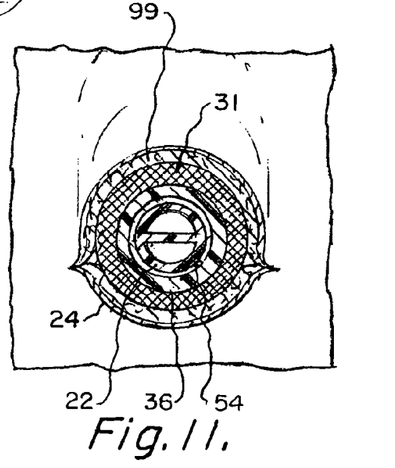
FIG. 11 is a sectional view showing the assembly of FIG. 5 accommodated in the stretched opening of FIG. 10.
Figure 14:
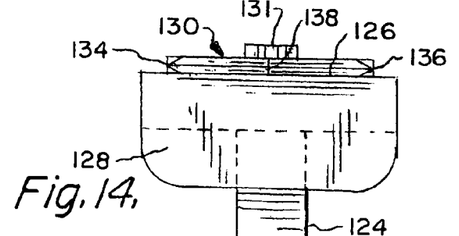
FIG. 14 is an end view of the cutting tool of FIG. 13.
Figure 15:
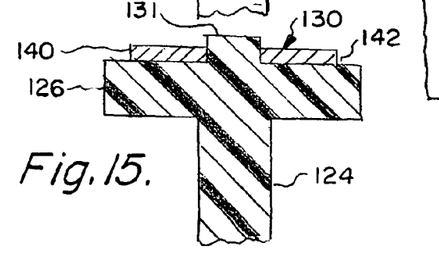
FIG. 15 is a sectional view taken substantially along the plane 15-15 of FIG. 13.

FIG. 10 illustrates the aforementioned incision 24 dimensioned in accordance with a preferred embodiment of the present invention. That is, in accordance with the present invention, the incision 24 is formed to provide an opening 100 having a width which is 10% to 20% less than the lateral dimension D4, i.e., outer diameter of the porous layer 31. In order to insert the sleeve 30 into the opening 100, the physician typically manually stretches the tissue surrounding the opening to allow the tapered forward portion 40 to dilate and pass through the opening to place the porous layer 31 in contact with the patient's dermis 99. The physician can then terminate the manual stretching to allow the surrounding tissue to relax toward the porous layer 31. Even in this relaxed state, however, because the opening 100 is undersized relative to the lateral dimension of the porous layer 31, the surrounding tissue remains stressed, e.g., radially and/or circumferentially, which acts to enhance cell proliferation and ingrowth into the porous layer.

In order to assist the physician to form a closely dimensioned undersized opening in accordance with the invention, it is preferable to provide a surgical cutting tool having a cutting edge dimensioned to the desired opening size. FIGS. 10-15 illustrate one such preferred surgical cutting tool 120 for forming a closely dimensioned incision 24. The tool 120 is comprised of a handle 124 having a flat upper surface 126 defining a forward face 128. A blade 130 is mounted on the surface 126 using, for example, a surface protuberance 131 extending into a keyway in the blade. The blade 130 has a front end 132 projecting beyond the handle face 128 comprised of first and second substantially straight cutting edge portions 134, 136. The portions 134, 136 diverge rearwardly from a pointed end 138. The cutting edge portions 134, 136 extend rearwardly and blend into blade parallel sides 140, 142. The maximum width of the cutting edge portions, i.e., the spacing between sides 140 and 142, is selected to be between 80% and 90% of the lateral dimension of the device to be inserted.

In use, a physician will incise the patient's skin with the blade point 138 by pushing the blade straight inwardly until stopped by face 128. That is, the spacing between pointed end 138 and face 128 will define the depth (e.g., 0.39") of the incision 24 formed by the blade 130. By pushing straight inwardly, the physician is able to create a clean closely dimensioned incision 24 to form opening 100. Preferably the blade width is selected to be between about 80 and 90% of the lateral dimension of the device to be inserted. The physician will then manually stretch the skin around opening 100 and insert the dilating forward portion 40 to place porous layer 31 adjacent the patient's dermis. After placement and after termination of the manual stretching, the surrounding tissue will elastically retract against the porous layer but will remain physically stressed by the relatively oversized device. The residual stress, or tension, in the surrounding tissue acts to stimulate healing and promote tissue ingrowth into the porous layer 31. In addition to the effects of circumferential strain on cellular proliferation, extracellular matrix deposition, or hypoxic signaling upregulating angiogenic response, an undersized incision in accordance with the invention may decrease the volume of the underlying subcutaneous pocket thus stabilizing the implanted device and reducing foreign body response to movement of the device.

After initial implantation of the catheter 22, it is sometimes desirable to reposition the catheter for more effective treatment and/or to reduce patient discomfort. Such repositioning can involve slightly adjusting the position and/or orientation of the catheter distal end and is achieved by pivoting the locking member 33 to the unlocked position (FIG. 3) and then sliding the catheter into or out of the sleeve 30 and/or by rotating the catheter in the sleeve. When satisfied with the catheter positioning, the physician will then pivot the locking member 33 to the locked position shown in FIG. 2. The physician can then compress the locking member wall 82 around the catheter to frictionally engage the locking member inner surface 86 against the catheter outer surface 56 to prevent any subsequent catheter movement relative to the sleeve 30. This locked state can be maintained by tying suture thread 97 around the annular grove 96. Of course, the thread 97 can be readily cut when it is desired to release the locked state to allow the catheter to be repositioned and/or replaced.

It is further pointed out that with the locking member 33 in its unlocked position, an implanted catheter can be fully withdrawn through the sleeve proximal end for replacement by a new catheter. Although different techniques can be employed, it is contemplated that the physician will thread a guide wire through the old catheter prior to withdrawing it. The new catheter is then threaded along the guide wire and through the sleeve. When the new catheter is properly placed, the guide wire is typically withdrawn.

From the foregoing, it should now be understood that a catheter assembly has been provided particularly configured to facilitate the positioning, repositioning, and/or replacement of a percutaneously implanted catheter. Although only a limited number of structural embodiments have been described, it is recognized that various modifications and alterations will occur to persons skilled in the art which fall within the spirit and intended scope of the invention as defined by the appended claims

The invention claimed is:

1. A medical device assembly including:
    an elongate tubular sleeve adapted for percutaneous implantation having axially spaced distal and proximal ends, said sleeve including a forward portion located proximate to said distal end, a rearward portion located proximate to said proximal end, and a laterally oriented shoulder surface therebetween;
    said forward portion having a smooth outer surface increasing from a minimum lateral dimension of D1 near said distal end to a maximum lateral dimension of D2 near said shoulder surface for insertion through a patient's skin incision;
    said rearward portion including a section adjacent to said shoulder surface having a porous surface of maximum lateral dimension D4, where D4 is equal to or less than D2, for subcutaneous placement in contact with a patient's dermis for promoting soft tissue ingrowth;
    said tubular sleeve further having an axially extending inner surface surrounding an interior axial passageway;
    an elongate conduit comprising a peripheral wall having an axially extending outer surface;
    said conduit extending through said sleeve passageway for axial slidable movement with respect thereto; and
    a sealing device in said passageway peripherally contacting said conduit outer surface for preventing migration of deleterious material between said sleeve inner surface and said conduit outer surface.

2. The assembly of claim 1 wherein said porous surface comprises a layer of porous material mounted around said sleeve rearward portion.

3. The assembly of claim 1 further including:
    a locking member coupled to said sleeve selectively operable in an unlocked state for permitting axial movement of said conduit through said sleeve passageway and in a locked state for preventing axial movement of said conduit through said sleeve passageway.

4. The assembly of claim 1 further including:
    an anchor device for retaining said sleeve proximal end exteriorly to a patient's skin.

5. The assembly of claim 4 further including:
    a locking member mounted to said anchor device, said locking member being selectively operable in an unlocked state for permitting axial movement of said conduit through said sleeve passageway and in a locked state for preventing axial movement of said conduit through said sleeve passageway.

6. The assembly of claim 5 wherein said locking member comprises a longitudinally split ring defining first and second opposed edges configured to move apart to define said unlocked state and to move together to define said locked state; and
    a hinge member for hinging said split ring to said anchor device.

7. The assembly of claim 6 where said split ring is comprised of flexible plastic material.

8. The assembly of claim 6 wherein said hinge member comprises a strap of flexible plastic material.

9. A medical device assembly including:
    a tubular sleeve adapted for percutaneous implantation having a proximal end intended for exterior placement and a distal end intended for subcutaneous placement, said sleeve having an axially extending outer surface and an axially extending inner surface surrounding an interior passageway;
    an elongate conduit comprising a peripheral wall having an axially extending outer surface;
    said conduit extending through said sleeve passageway for axial slidable movement with respect thereto;
    a sealing device peripherally contacting said conduit outer surface for preventing migration of deleterious material between said sleeve inner surface and said conduit outer surface;
    a layer of porous material mounted around said sleeve outer surface adapted for subcutaneous placement in contact with a patient's dermis layer for promoting soft tissue ingrowth;
    an anchor device configured to engage said sleeve to retain said sleeve proximal end exteriorly to a patient's skin;
    a longitudinally split ring;
    a hinge member coupling said split ring to said anchor device for allowing said split ring to move between a first position surrounding said conduit and a second position remote from said conduit; and
    means for compressing said split ring in said first position for preventing axial movement of said conduit through said sleeve passageway.

10. The assembly of claim 9 wherein said sealing device comprises an annular seal defining an interior bore having a flexible annular nib for engaging said conduit outer surface.

11. The assembly of claim 9 wherein said layer of porous material incorporates antimicrobial and/or anti-inflammatory agents.

12. The assembly of claim 9 wherein said sleeve is formed of rigid material.

13. The assembly of claim 9 wherein said sleeve is formed of flexible material.

14. The assembly of claim 9 wherein said means for compressing said split ring comprises thread.

15. The assembly of claim 9 wherein said means for compressing said split ring comprises a spring clip.

16. The assembly of claim 9 wherein said sleeve outer surface defines a lateral shoulder surface between said proximal end and said distal end;

said sleeve outer surface has a lateral dimension which increases from D1 near said distal end to D2 near said shoulder surface; and wherein said layer of porous material is mounted between said shoulder surface and said proximal end and has a maximum lateral dimension D4 where D4 is equal to or less than D2.

* * * * *